US00PP28657P3

(12) United States Plant Patent
Radler

(10) Patent No.: US PP28,657 P3
(45) Date of Patent: Nov. 21, 2017

(54) CLIMBING ROSE PLANT NAMED 'RADPETALS'

(50) Latin Name: *Rosa hybrida*
Varietal Denomination: Radpetals

(71) Applicant: THE CONARD-PYLE COMPANY, West Grove, PA (US)

(72) Inventor: William J. Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 14/757,789

(22) Filed: Dec. 29, 2015

(65) Prior Publication Data

US 2017/0188493 P1 Jun. 29, 2017

(51) Int. Cl.
*A01H 5/02* (2006.01)

(52) U.S. Cl.
USPC ..... Plt./113

(58) Field of Classification Search
USPC ..... Plt./113, 109
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct Climbing rose plant is provided that abundantly and substantially continuously forms attractive semi-double cup-shaped coral blossoms with yellow eyes. The plant exhibits vigorous and strong vegetation. The foliage is ornamental dark green with a semi-glossy finish on the upper surface. The lighter blossom coloration contrasts nicely with the dark green foliage. The disease resistance is excellent, particularly with respect to black spot, rust and mildews. The plant is well suited for providing attractive ornamentation.

2 Drawing Sheets

Botanical/commercial classification: *Rosa hybrida*/ Climbing Rose Plant.

Varietal denomination: cv. Radpetals.

SUMMARY OF THE INVENTION

The new variety of *Rosa hybrida* Climbing rose plant of the present invention was created in June 2005 at Greenfield, Wis., U.S.A., by artificial pollination wherein two parents were crossed which previously had been studied in the hope that they would contribute the desired characteristics. The female parent (i.e., seed parent) was the 'Radbig' variety (non-patented and unreleased breeder seedling), and the male parent (i.e., pollen parent) was the 'Radfourth' variety (non-patented and unreleased breeder seedling). The parentage can be summarized as follows:

'Radbig'×'Radfourth'.

The seeds resulting from the above pollination were sown and small plants were obtained which were physically and biologically different from each other. Selective study resulted in the identification of a single plant of the new variety.

It was found that the new Climbing rose plant of the present invention possesses the following combination of characteristics:

(a) abundantly and substantially continuously forms attractive semi-double cup-shaped coral blossoms with yellow eyes,
(b) exhibits a very bushy and climbing growth habit,
(c) forms vigorous and strong vegetation,
(d) forms attractive ornamental dark green foliage with a semi-glossy finish on the upper surface that contrasts well with the blossom coloration, (e) exhibits excellent disease resistance particularly with respect to black spot, rust and mildews, and
(f) is well suited for providing attractive ornamentation.

A new rose variety is provided displaying attractive cup-shaped coral blossoms with yellow eyes combined with substantially continuous blossoming and excellent disease resistance.

The new variety well meets the needs of the horticultural industry. It can be grown to advantage as ornamentation in parks, gardens, public areas, and in residential settings to cover a trellis, arbor or fence. Accordingly, the plant is particularly well suited for growing in the landscape where a climbing rose plant is desired.

The new variety can be readily distinguished from its ancestors upon an inspection of the blossoms. More specifically, the 'Radbig' parent variety forms dissimilar single blossoms having only five petals, and the 'Radfourth' variety forms dissimilar double blossoms combined with a shrub growth habit.

The new variety also can be readily distinguished from the 'Radbrite' variety (U.S. Plant Pat. No. 17,391) through an inspection of the blossoms. More specifically, the 'Radbrite' variety displays dissimilar single blossoms having only approximately seven to ten petals.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radpetals', and will be marketed under the FRUITY PETALS Trademark.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately three years of age and were observed during May 2012 while growing outdoors on their own roots at West Grove, Pa., U.S.A.

DETAILED BOTANICAL DESCRIPTION

Figure 1:
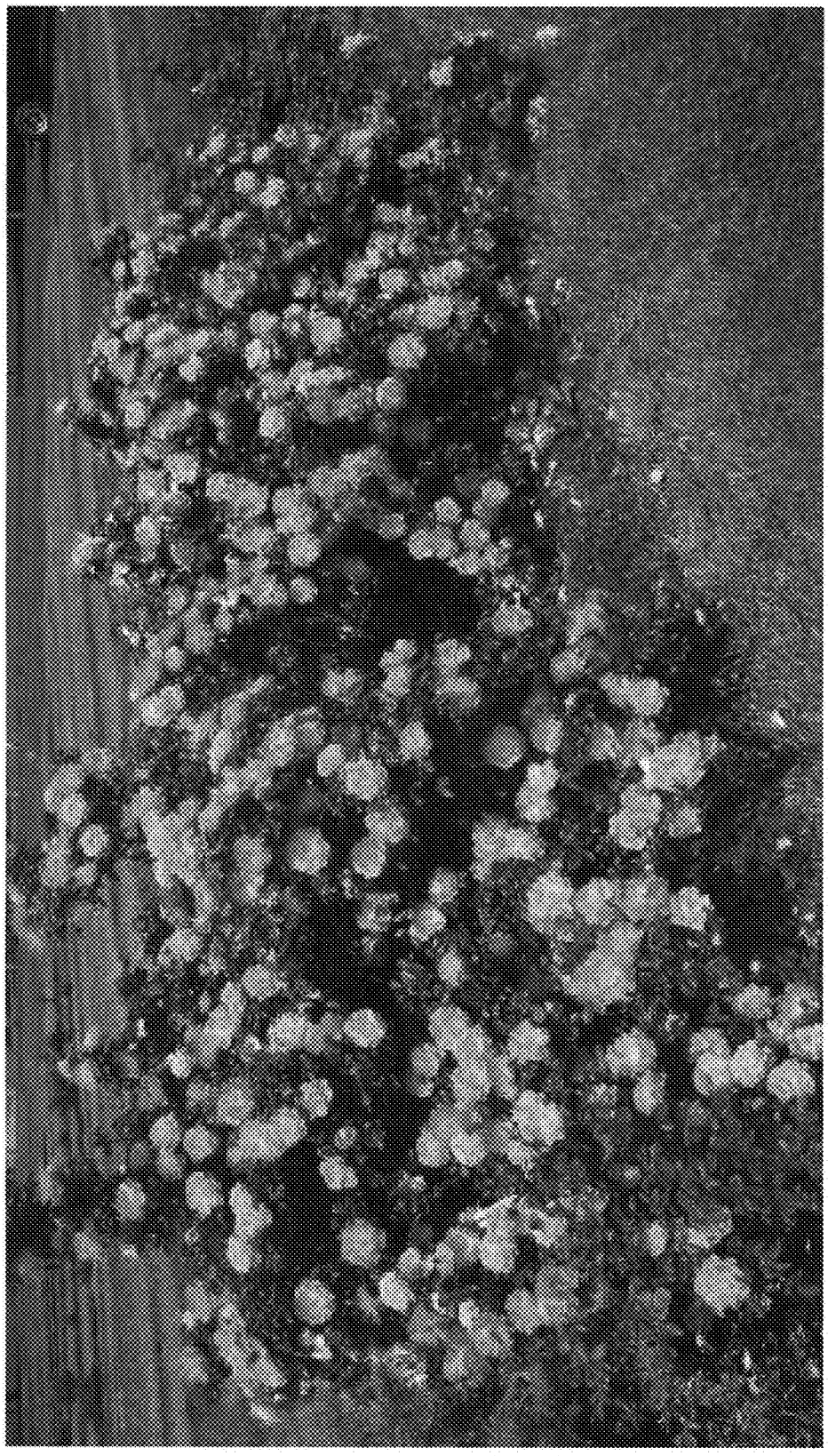
FIG. 1 shows a row of flowering plants of the new variety.
Figure 2:
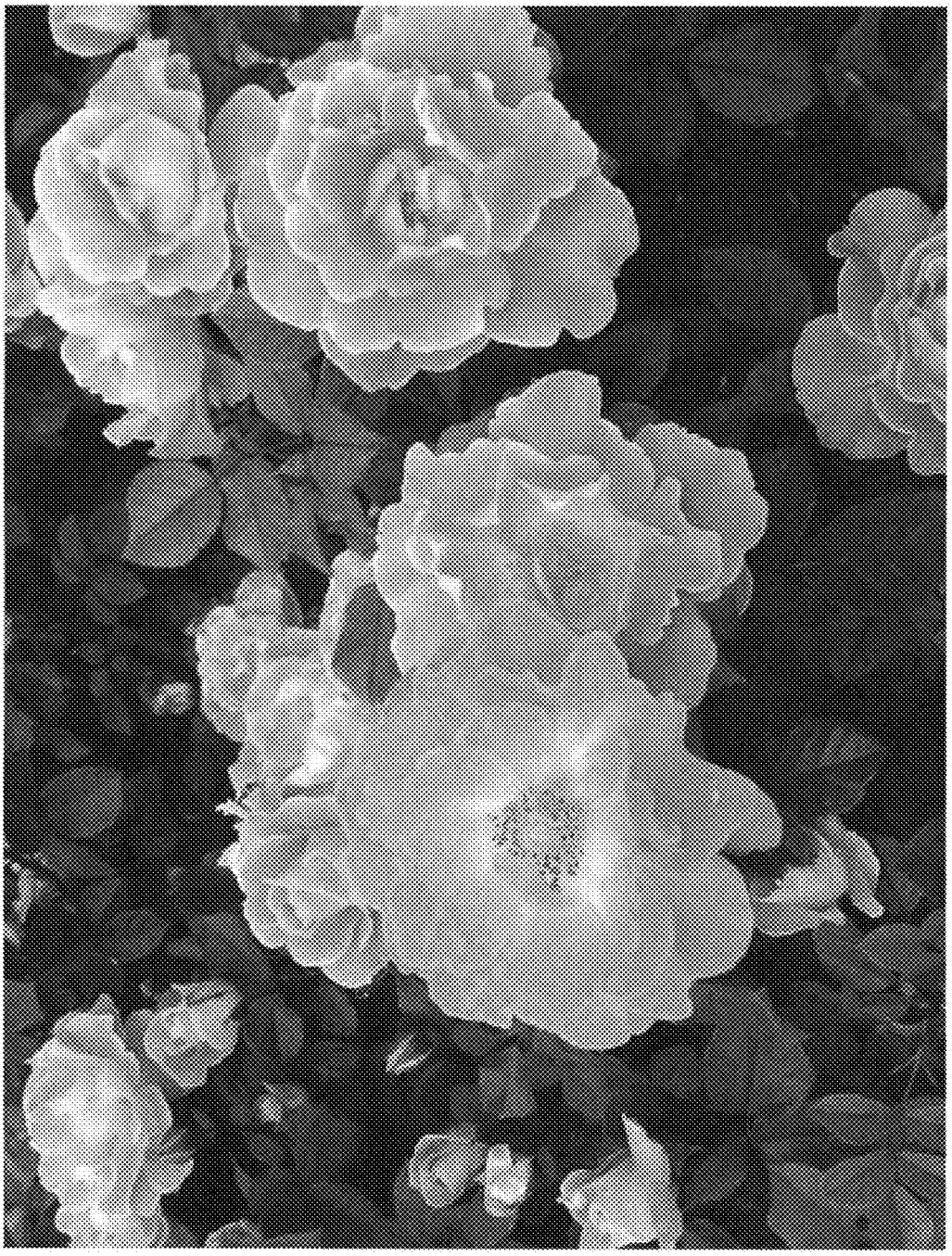
FIG. 2 shows a closer view of the blossoms in various stages of development and foliage of the new variety.

The chart used in the identification of colors is that of The Royal Horticultural Society (R.H.S. Colour Chart—1995 Edition), London, England. The description is based on the observation of two-year-old specimens of the new variety during August while growing in containers on their own roots at West Grove, Pa., U.S.A.

Class: Climbing Rose.

Variety: 'Radpetals'.

Plant:

*Height*.—Commonly up to approximately 1.8 m on average of growth.

*Width*.—Commonly approach approximately 90 cm on average.

*Habit*.—Bushy and climbing.

Stems:

*Length*.—Main stems commonly approximately 9 cm on average, and secondary stems commonly approximately 30 cm on average.

*Diameter*.—Main stems commonly approximately 1.5 cm on average, and secondary stems commonly approximately 0.5 cm on average.

*Color*.—Near Yellow-Green Group 148B mixed with Greyed-Brown Group 183A on young stems, and commonly near Yellow-Green Group 146A mixed with some Greyed-Brown Group 199B on old wood.

*Thorns*.—Size: commonly approximately 1.3 cm in length on average and approximately 8 mm in width on average at the point of attachment when young, and approximately 1.1 cm in length on average and approximately 7 mm in width on average at the point of attachment when old. Color: commonly near Green-Purple Group 183B on young stems, and near Greyed-Green Group 197C when old.

Leaves:

*Size*.—Commonly approximately 9.5 cm in length on average, and approximately 8 cm in width on average for a five-leaflet leaf.

*Petioles*.—Commonly approximately 1.5 cm in length on average, commonly approximately 1.0 mm in diameter on average, and color is commonly near Yellow-Green Group 144A.

*Rachis*.—Commonly approximately 3.0 cm in length on average, commonly approximately 1.0 mm in diameter on average, and color is commonly near Yellow-Green Group 144A.

*Leaflets*.—Number: 3, 5, and 7. Length: approximately 5 cm on average for a terminal leaflet, and approximately 4 cm on average for a lower leaflet. Width: approximately 3.5 cm on average for a terminal leaflet, and approximately 2.5 cm on average for a lower leaflet. Shape: generally ovate with an acuminate apex and rounded base. Margins: serrate. Texture: generally smooth on the upper and under surfaces. Overall appearance: vigorous and strong with attractive ornamental dark green leaves with a semi-glossy upper surface. Color: (when young): Upper surface: near Yellow-Green Group 148A. Under surface: near Yellow-Green Group 146B. Color (when fully mature): Upper surface: near Green Group 137A. Under surface: near Yellow-Green Group 147B.

Inflorescence:

*Number of flowers*.—Commonly singly or in a cluster of approximately 2 to 4 blossoms on average per stem, and commonly with approximately 20 blossoms on average being present on the plant at a given time.

*Peduncle*.—Near Yellow-Green Group 144A overlaid with Red-Purple Group 59A in coloration, commonly approximately 3.5 cm in length on average, approximately 2.5 mm in diameter on average, and commonly sparsely covered with small flexible thorns less than 2 mm in length.

*Sepals*.—Upper surface: covered with short pubescence, and commonly near Green Group 138B in coloration. Under surface: commonly puberulent, and commonly near Yellow-Green Group 144A in coloration. Size: commonly approximately 1.9 cm in length on average, and approximately 9 mm in width at the base. Shape: generally ovate with an aristate apex. Margin: entire, and commonly with an extension on two or three of the sepals measuring approximately 3 mm in length on average and approximately 1 mm in width on average. Number: five.

*Buds*.—Shape: generally ovoid. Length: approximately 2 cm on average as the calyx breaks. Diameter: approximately 1.5 cm on average as the calyx breaks. Color: when opening near Red Group 51B towards the apex blending to Yellow Group 13B at the base.

*Flower*.—Form: semi-double, cuplike. Depth: commonly approximately 3.0 cm on average. Diameter: commonly approximately 8 cm on average when fully open. Color (when opening begins): Upper surface: near Yellow Group 9C at the point of attachment transitioning to near Red Group 54A towards at the apex. Under surface: near Yellow Group 9A at the point of attachment transitioning to near Orange Group 24D towards the apex. Color (at end of blooming): Upper surface: near Yellow Group 5C at the point of attachment transitioning to near Red Group 51A towards the apex. Under surface: near Yellow Group 8B at the point of attachment transitioning to near Yellow-Orange Group 19A towards the apex. Fragrance: slight. Petal number: commonly approximately 18 on average under normal growing conditions. Petal length: commonly approximately 3 cm on average. Petal width: commonly approximately 3.5 cm on average. Petal shape: broadly obovate. Petal margin: entire. Petal apex: slightly cuspidate. Petal base: cuneate. Margin: entire. Petal drop: good, the petals commonly detach cleanly and freely drop upon full maturity. Stamen number: approximately 80 on average. Anthers: commonly near Yellow-Orange Group 17B in coloration. Filaments: approximately 7 mm in length, and the coloration is near Yellow Group 13A. Pollen: commonly present in a moderate quantity, and near Yellow-Orange Group 21A in coloration. Pistils: separate and free, and commonly number approximately 50 on average. Styles: commonly approximately 1 cm in length and near Red Group 47A at the tip and near Yellow-Green Group 145B at the base. Stigma: commonly approximately 1 mm in diameter on average, and near Yellow Group 13B in coloration. Receptacle: commonly substantially round in shape, approximately 9 mm in diameter, smooth in texture, near Yellow-Green Group 144A in coloration, and with achenes commonly being present on the bottom and wall.

Development:

*Vegetation*.—Dark green vigorous, and strong.

*Blossoming*.—Abundant and substantially continuous from spring to frost; a bloom stays on the plant for approximately 4 to 5 days on average.

*Resistance to diseases*.—Excellent, particularly with respect to black spot, rust, and mildews. Plants of the 'Radpetals' variety have not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive semi-double cup-shaped coral blossoms with yellow eyes, (b) exhibits very bushy and climbing growth habit, (c) forms vigorous and strong vegetation, (d) forms attractive ornamental dark green foliage with a semi-glossy finish on the upper surface that contrasts well with the blossom coloration, (e) exhibits excellent disease resistance particularly with respect to black spot, rust and mildews, and (f) is well suited for providing attractive ornamentation; substantially as herein shown and described.

* * * * *